(12) United States Patent
German et al.

(10) Patent No.: US 7,175,665 B2
(45) Date of Patent: Feb. 13, 2007

(54) UNIVERSAL TIBIAL AUGMENT

(75) Inventors: Deborah S. German, Plymouth, IN (US); Jeffrey L. Koenneman, Plymouth, IN (US)

(73) Assignee: Depuy Products, Inc., Warsaw, IN (US)

( * ) Notice: Subject to any disclaimer, the term of this patent is extended or adjusted under 35 U.S.C. 154(b) by 564 days.

(21) Appl. No.: 10/641,721

(22) Filed: Aug. 15, 2003

(65) Prior Publication Data
US 2004/0049284 A1    Mar. 11, 2004

Related U.S. Application Data

(60) Provisional application No. 60/409,319, filed on Sep. 9, 2002.

(51) Int. Cl.
*A61F 2/38* (2006.01)
(52) U.S. Cl. .................................. 623/20.15
(58) Field of Classification Search .. 623/20.14–20.36, 623/23.39, 23.42, 18.11; 606/88
See application file for complete search history.

(56) References Cited

U.S. PATENT DOCUMENTS

| 4,944,757 A | 7/1990 | Martinez |
| 4,944,760 A * | 7/1990 | Kenna ........................ 128/898 |
| 5,019,103 A | 5/1991 | Van Zile |
| 5,047,058 A | 9/1991 | Roberts |
| 5,370,693 A | 12/1994 | Kelman |
| 5,776,134 A * | 7/1998 | Howland .................... 606/61 |
| 6,139,581 A | 10/2000 | Engh |
| 6,214,052 B1 | 4/2001 | Burkinshaw |

* cited by examiner

*Primary Examiner*—Eduardo C. Robert
*Assistant Examiner*—David Comstock

(57) ABSTRACT

A prosthetic knee system has a tibial component and a universal augment. A single augment can be used to support the tibial tray on either the medial or lateral side. The augment has reverse image sides and a through-bore with no threads. The tibial tray has a complementary threaded bore. The through-bore of the augment has a plane of symmetry perpendicular to its central longitudinal axis.

10 Claims, 6 Drawing Sheets

UNIVERSAL TIBIAL AUGMENT

This application claims the benefit of U.S. Provisional Application No. 60/409,319, entitled "Universal Tibial Augment", filed on Sep. 9, 2002, by Deborah S. German and Jeffrey L. Koenemann, which is incorporated by reference herein in its entirety.

BACKGROUND OF THE INVENTION

The present invention relates generally to prosthetic joints and, more particularly, to a modular tibial augment for prosthetic knee joints. The tibial augment may be used to compensate for a broad range of types and sizes of bone deficiencies.

The knee joint basically consists of the bone interface of the distal end of the femur and the proximal end of the tibia. Appearing to cover or at least partially protect this interface is the patella which is a sesamoid bone within the tendon of the long muscle (quadriceps) on the front of the thigh. This tendon inserts into the tibial tuberosity and the posterior surface of the patella is smooth and glides over the femur.

The femur is configured with two knob like processes (the medial condyle and the lateral condyle) which are substantially smooth and articulate with the medial plateau and the lateral plateau of the tibia, respectively. The plateaus of the tibia are substantially smooth and slightly cupped thereby providing a slight receptacle for receipt of the femoral condyles.

When the knee joint is injured whether as a result of an accident or illness, a prosthetic replacement of the damaged joint may be necessary to relieve pain and to restore normal use to the joint. Typically the entire knee joint is replaced by means of a surgical procedure which involves removal of the ends of the corresponding damaged bones and replacement of these ends with prosthetic implants. This replacement of a native joint with a prosthetic joint is referred to as a primary total-knee arthroplasty.

On occasion, the primary knee prostheses fails. Failure can result from many causes, including wear, aseptic loosening, osteolysis, ligamentous instability, arthrofibrosis and patellofemoral complications. When the failure is debilitating, revision knee surgery may be necessary. In a revision, the primary knee prosthesis is removed and replaced with components of a revision prosthetic knee system.

In revision knee surgery or arthroplasty, bone loss on the proximal tibia can make it difficult to properly position and support the tibial component of the revision system on the proximal tibial surface. The prior art has addressed this problem by providing tibial wedges. Generally, the tibial wedges are placed between part of the distal surface of the tibial tray component and part of the proximal tibia to support part of the tibial tray on the tibia by augmenting part of the tibia. An example of such a tibial wedge is disclosed in U.S. Pat. No. 5,019,103.

Due in part to the fact that the size, shape and anatomy of virtually every patient is different, and the variability in the location and amount of bone loss on the proximal tibia, an extensive number of a variety of tibial wedges have been made available to the orthopedic surgeon. For example, a typical surgical kit will include tibial wedges of different thicknesses and different configurations for use on either the medial or lateral sides of the tibial.

Examples of components of two revision knee systems are illustrated in FIGS. 1–9. The components illustrated in FIGS. 1–5 are part of one prior art revision knee system, and the components illustrated in FIGS. 6–9 are part of a second prior art revision knee system. Both include tibial components 10 comprising tibial trays 12 and tibial stems 14. The tibial stems 14 extend out from the distal side 16 of the tibial tray 12. Each tibial tray 12 is symmetrical about a central plane 18 that divides the tray into a medial side 20 and a lateral side 22. The medial and lateral sides 20, 22 are mirror images of each other.

In the prior art components illustrated in FIGS. 1–5, the tibial tray 12 has two threaded through-bores, 24, 26, one on the medial side 20 and one on the lateral side 22. The threaded through-bores 24, 26 extend from the distal surface 16 to the proximal surface 28 of the tibial tray 12. These threaded through-bores 24, 26 are provided for the selective mounting of a tibial wedge or augment element to the distal side 16 of the tibial tray.

Tibial augment or wedge components for the prior system of FIGS. 1–5 are illustrated in FIGS. 4–5. The two tibial augments or wedges 30, 32 are mirror images of each other. Each has a proximal surface or side 34 that is juxtaposed with the distal side 16 of the tibial tray when the augment or wedge is mounted on the tray and a distal side or surface 36 that is intended to be juxtaposed with a resected tibial surface when implanted. Each illustrated augment or wedge 30, 32 has an outer edge 37, 38 shaped to follow a portion of the outer edge 40 of the tibial tray 12. Each augment or wedge 30, 32 also has a smooth through-bore 42, 44 extending from the distal surface 36 to the proximal surface 34 of the augment or wedge 30, 32. A typical through-bore 42, 44 for each augment or wedge is illustrated in cross-section in FIG. 5. As there shown, each smooth through-bore 42, 44 has a large diameter countersink 46 extending from the distal surface 36 toward the proximal surface 34 and a small diameter neck 48 at the proximal end of the countersink 46. In the system of FIGS. 1–5, the small diameter neck 48 is defined by a smooth surface. On the proximal surface 34, each through-bore 42, 44 includes an enlarged undercut 50. The augments or wedges 30, 32 can be mounted to the distal side 16 of the tibial tray 12 with screws (not shown); the heads of the screws are received in the countersinks 46, and the threaded screw shaft extends through the reduced diameter neck 48 to engage the threads of the threaded through-bores 24, 26 of the tibial tray 12. With the through-bores shaped as illustrated in FIG. 5, the augments or wedges 30 of FIG. 3 can only be mounted on one side of the central plane 18 of the tibial tray 12, on the side shown at 22 in FIG. 2. Similarly, the augment or wedge 32 shown in FIG. 4 can only be mounted on the other side of the central plane 18 of the tibial tray 12, on the side shown at 20 in FIG. 2.

Since each augment or wedge 30, 32 can only be mounted on one side of the central plane 18 of the tibial tray 12, it is necessary to provide two complete sets of augments or wedges in a typical surgical kit, one set for use on the medial side and one set for use on the lateral side. Each of these sets would typically include at least two different thicknesses of tibial augments or wedges. The typical surgical kit would also typically include several different sizes of tibial augments or wedges 30, 32, corresponding to the sizes of tibial trays provided. Thus, a substantial number of augments or wedges 30, 32 are needed in the revision system of FIGS. 1–5.

A substantial number of augments or wedges 30, 32 are also needed in the revision system of FIGS. 6–9. In the system of FIGS. 6–9, like reference numbers have been used for similar parts. In this prior art system, the tibial stem 14 and distal side 16 of the tibial tray 12 are connected by keels 52. Each augment or wedge 30, 32 includes two threaded through-bores 54, 56 and a cut-out 58 to complement and receive one of the keels 52. Each of the two sides 20, 22 of the tibial tray 12 has two threaded bores 58, 60 to be aligned with the threaded through-bores 54, 56 of one of the augments 30, 32. As shown in FIG. 9, each threaded through-bore 54, 56 of each augment has a proximal and distal countersink 62, 64 and an elongate threaded neck 66. To mount one of the augments or wedges 30, 32 on the tibial tray 12, a screw is threaded through each threaded through-bore 54, 56 of the augment and threaded into the threaded bore 58, 60 of the distal side 16 of the tibial tray 12.

Since the through-bores 54, 56 of the augments 30, 32 are threaded, each augment 30 or 32 can only be mounted on one side of the central plane 18 dividing the tray 12 into medial and lateral portions 20, 22. Since each augment or wedge 30, 32 can only be mounted on one side of the central plane 18 of the tibial tray 12, it is also necessary to provide two complete sets of augments or wedges in a typical surgical kit for the system of FIGS. 6–9, one set for use on the medial side and one set for use on the lateral side. Each of these sets would also typically include at least two different thicknesses of tibial augments or wedges. The typical surgical kit would also typically include several different sizes of tibial augments or wedges 30, 32, corresponding to the sizes of tibial trays provided. Thus, a substantial number of augments or wedges 30, 32 are needed in the revision system of FIGS. 6–9.

The need for a large number of augments or wedges in the surgical systems of the prior art adds substantially to the cost of these systems.

SUMMARY OF THE INVENTION

The present invention addresses the need for greater economy in prosthetic knee systems. In one aspect, the present invention addresses this need by providing a universal tibial augment comprising a first side, a second side opposite the first side, a thickness between the first side and the second side and a through-bore extending from the first side to the second side. The through-bore is smooth from the first side to the second side.

In another aspect, the present invention addresses this need by providing a universal tibial augment comprising a first surface, a second surface and a thickness between the first surface and the second surface. The universal tibial augment has a through-bore extending from the first surface to the second surface. The through-bore has a central longitudinal axis and includes a first countersink at the first surface, a second countersink at the second surface and a smooth neck connecting the first and second countersinks. The augment includes inner tapered surfaces defining the first and second countersinks and a smooth inner cylindrical surface defining the neck. The shape and dimensions of the inner tapered surfaces defining the first and second countersinks are substantially the same.

In another aspect, the present invention addresses this need by providing a prosthetic tibial system comprising a tibial tray and a universal tibial augment. The tibial tray has a proximal side, a distal side and a stem extending outward from the distal side. The tibial tray has a plane of symmetry extending through the stem and the proximal side, and includes a threaded bore on each side of the plane of symmetry extending from the distal side toward the proximal side. The tibial augment has a first side, a second side opposite the first side, a thickness between the first side and the second side and a through-bore extending from the first side to the second side. The tibial augment is mountable on the distal surface of the tibial tray on both sides of the plane of symmetry of the tibial tray.

BRIEF DESCRIPTION OF THE DRAWINGS

In the following drawings like reference numbers are used for like parts.

DETAILED DESCRIPTION OF THE INVENTION

Figure 1:
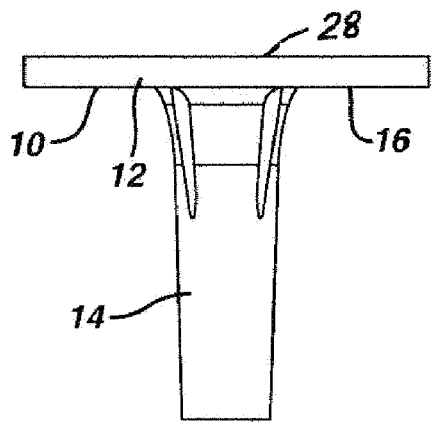
FIG. 1 is a front elevation of a prior art prosthetic tibial component.
Figure 2:
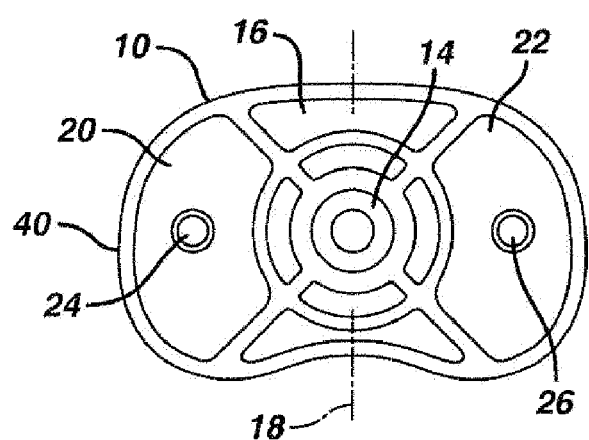
FIG. 2 is a bottom plan view of the tibial component of FIG. 1, showing the distal surface of the tibial tray.
Figure 3:
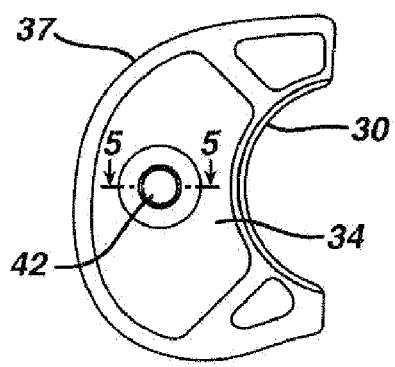
FIG. 3 is a top plan view of a prior art tibial augment for use on one side of the central plane of the prior art tibial tray of FIGS. 1–2.
Figure 4:
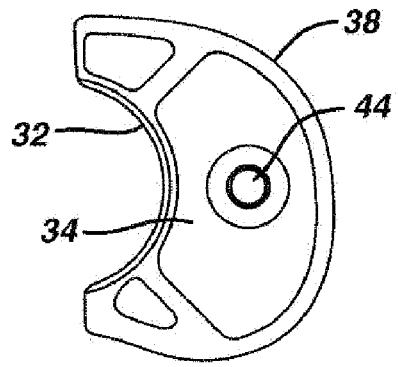
FIG. 4 is a top plan view of a prior art tibial augment for use on the opposite side of the central plane of the prior art tibial tray of FIGS. 1–2.
Figure 5:
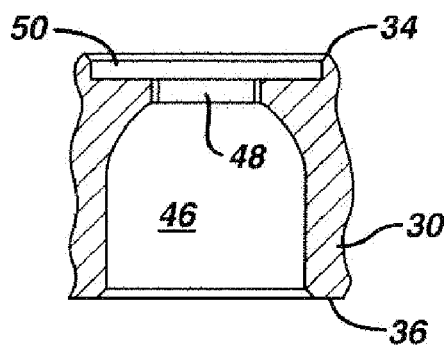
FIG. 5 is a cross-section taken along line 5—5 of FIG. 3.
Figure 6:
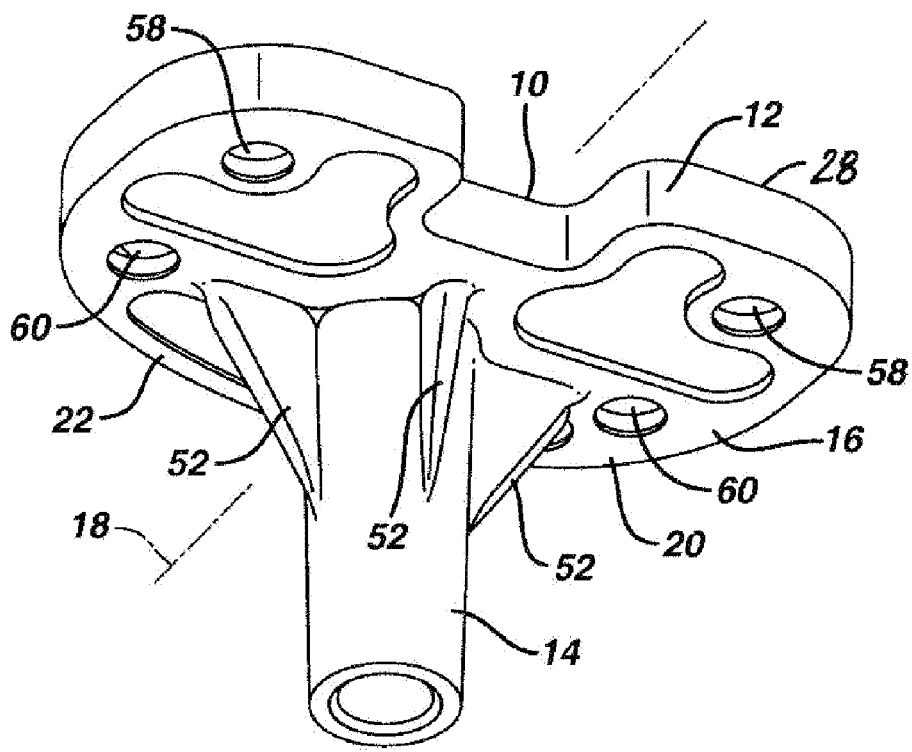
FIG. 6 is a perspective view of another prior art prosthetic tibial component.
Figure 7:
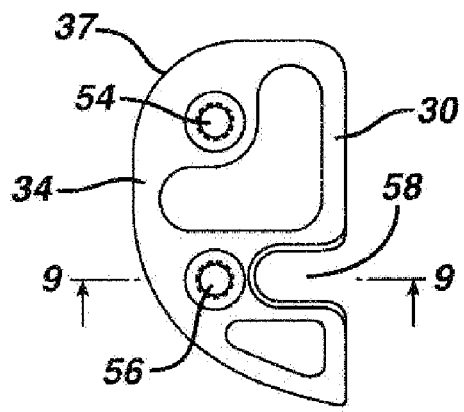
FIG. 7 is a top plan view of a prior art tibial augment for use on one side of the central plane of the prior art tibial tray of FIG. 6.
Figure 8:
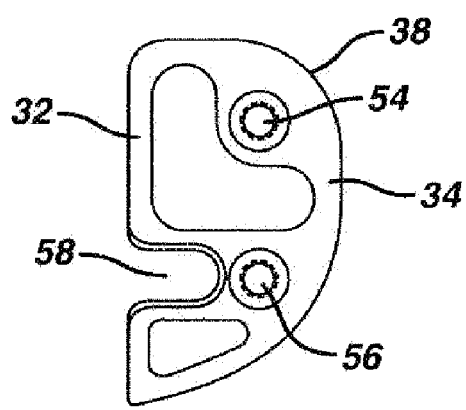
FIG. 8 is a top plan view of a prior art tibial augment for use on the other side of the central plane of the prior art tibial tray of FIG. 6.
Figure 9:
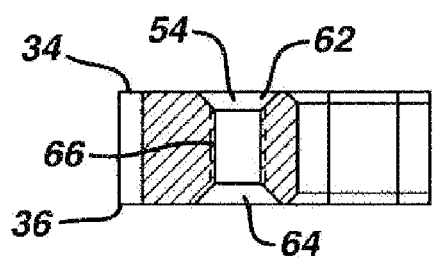
FIG. 9 is a cross-section taken along line 9—9 of FIG. 7.

A prosthetic tibial system 10 incorporating the principles of the present invention is illustrated in FIGS. 10–16. The prosthetic tibial system 100 is a modular one, including a tibial component 102, a tibial augment 104 and a stem extension 106. It should be understood that the tibial system 100 will probably include multiple sizes of each of these components so that the surgeon can select the most appropriate size components for each patient.

Figure 10:
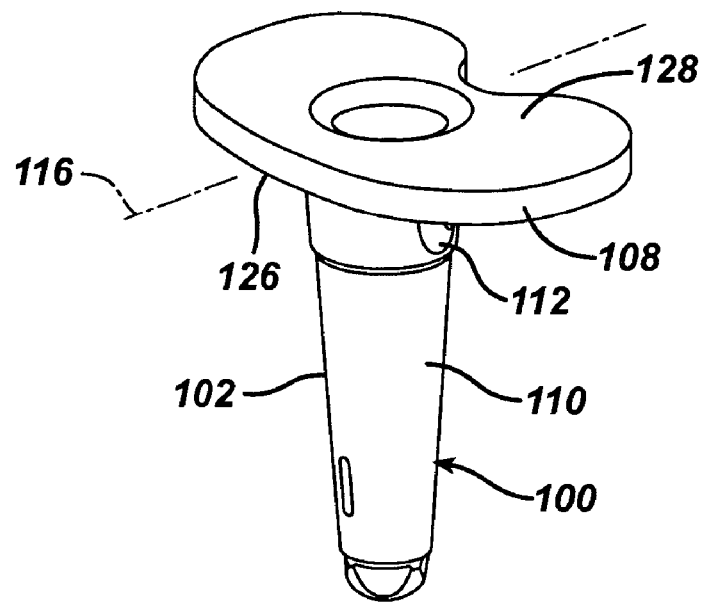
FIG. 10 is a perspective view of a tibial component of the prosthetic knee system of the present invention.
Figure 11:
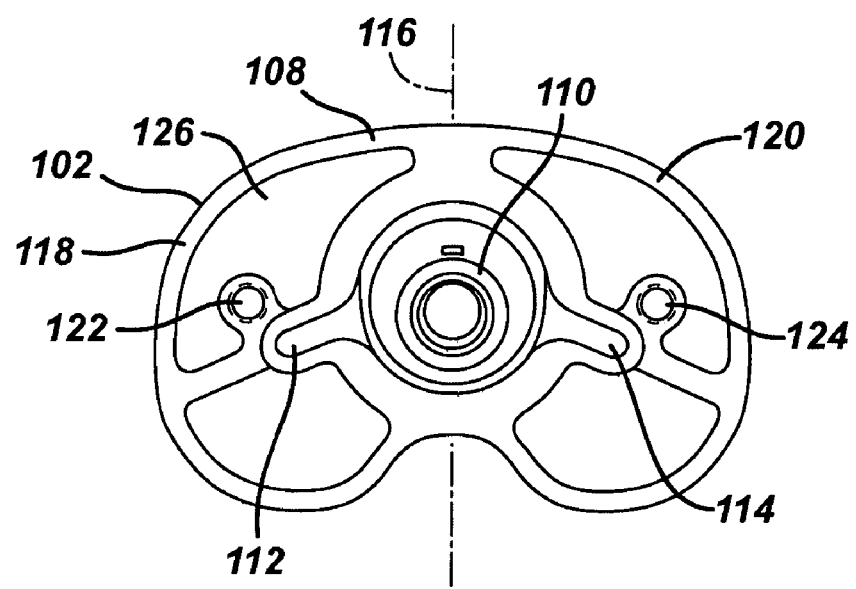
FIG. 11 is a bottom plan view of the tibial tray and tibial stem of the tibial component of FIG. 10.

As shown in FIGS. 10–11, the tibial component 102 includes a tibial tray 108 and an integral tibial stem 110. A pair of keels 112, 114 extend between and are integral with the tibial stem 110 and tibial tray 108. The stem extension 106 is provided for mounting into the intramedullary canal, as known in the art.

The tibial tray 108 has a central longitudinal plane 116 that divides the tray into symmetrical medial and lateral portions, designated 118 and 120 in FIG. 11. Each of the symmetrical portions 118, 120 has a closed-ended, threaded bore 122, 124, open at the distal side or surface 126 of the tray 108 and extending toward the proximal side or surface 128.

Figure 12:
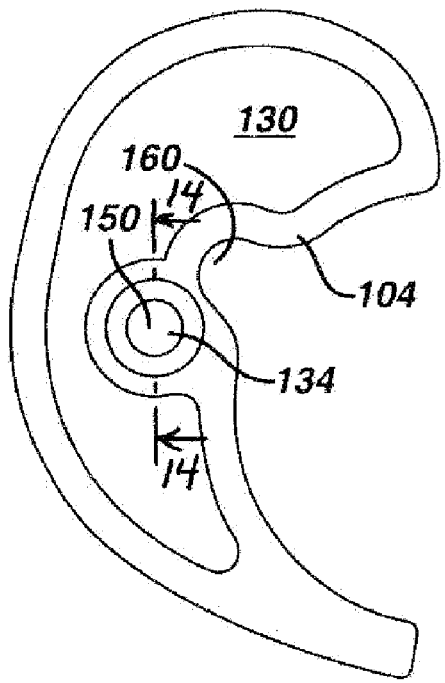
FIG. 12 is a top plan view of an embodiment of the universal tibial augment of the present invention.
Figure 13:
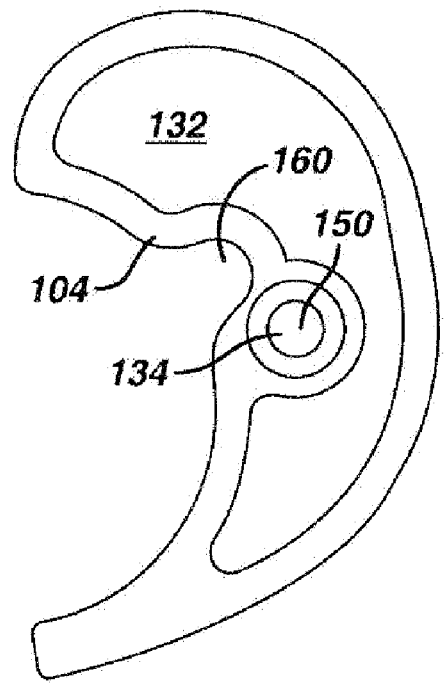
FIG. 13 is a bottom plan view of the universal tibial augment of FIG. 12.

The illustrated universal tibial augment 104 has a first side or surface 130 shown in FIG. 12, a reverse image second side or surface 132 shown in FIG. 13, and a thickness 133 between these sides 132, 134. The illustrated tibial augment or wedge 104 is reversible so that a single augment or wedge 104 can be used to supplement either the medial or lateral side of the tibial tray 108. The illustrated tibial augment or wedge 104 is reversible not only because the first and second sides or surfaces 130, 132 are reverse images of each other, but also because of the unique mounting mechanism provided by the present invention. It should be understood that the present invention is not limited to reversible tibial augments unless expressly called for in the claims.

Figure 14:
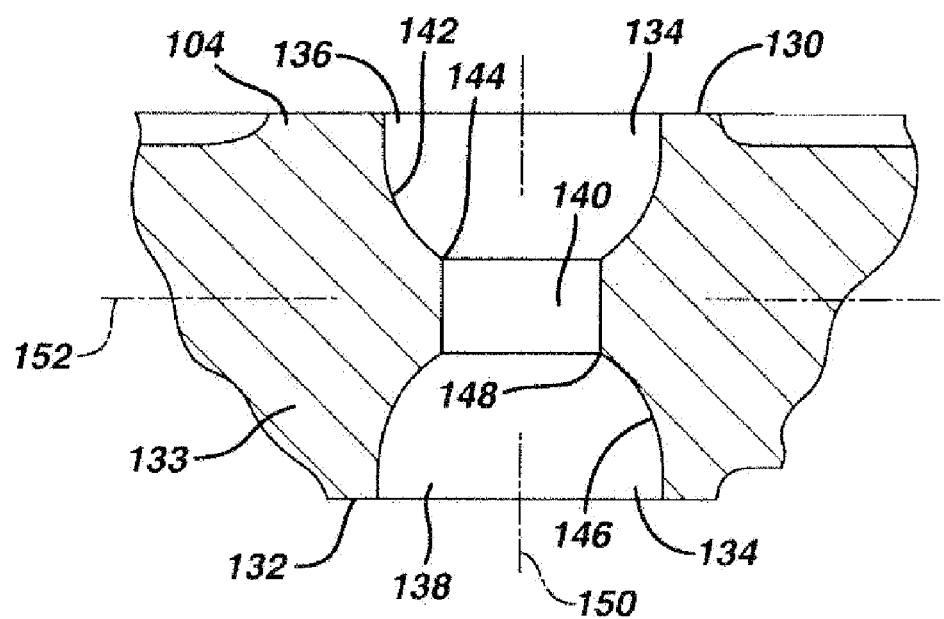
FIG. 14 is a cross-section taken along line 14—14 of FIG. 12.

The universal tibial augment 104 has a smooth through-bore 134 for mounting the augment or wedge 104 to the distal side or surface 126 of the tibial tray 108. As shown in FIG. 14, the illustrated through-bore 134 has a general hour-glass shape, with a first countersink 136 and a second countersink 138 connected by a reduced-diameter neck 140. However, it should be understood that the invention is not limited to any particular shape of through-bore unless expressly called for in the claims.

As shown in FIG. 14, the first countersink 136 has an enlarged outer diameter at the first surface 130, and is defined by an inner concave curved surface 142 that tapers to a reduced inner diameter at the juncture 144 of the countersink 136 and neck 140. The second countersink 138 has an enlarged outer diameter at the second surface 132, and is defined by an inner concave curved surface 146 that tapers to a reduced inner diameter at the juncture 148 of the countersink 138 and neck 140. The neck 140 has the smallest diameter of the through-bore 134. The inner surface 141 of the augment defining the neck 140 comprises a smooth, cylindrical surface; the inner surface 141 is not threaded and the countersinks 136, 138 are not threaded, so that the entire through-bore 134 is smooth, that is, not threaded.

The through-bore 134 has a central longitudinal axis 150 and is symmetrical about a plane 152 perpendicular to the central longitudinal axis 150 and lying between the first and second surfaces or sides 130, 132 of the tibial augment 104.

The augment 104 also includes a cut-out 160 to clear the keels 112, 114 of the tibial component 102, and also to serve as an anti-rotation feature.

In the illustrated embodiment, the tibial augment 104 comprises a block with substantially parallel surfaces 130, 132. The principles of the present invention are also applicable to other shapes of augments, such as wedge shapes, and the invention is not limited to any particular shape of augment unless expressly called for in the claims. Thus, although the illustrated tibial augment has a curved outer edge corresponding to the curve of the outer edge of the tibial tray, the tibial augment can have a different shape than that shown, and the shape of the augment need not correspond with the shape of the tibial tray.

In the system of the invention, it is expected that several different sizes of tibial components 102 will be supplied in a single surgical kit to accommodate differences in patient anatomy. Rather than make each size of tibial component 102 exactly proportional to the other sizes, it may be desirable to make the geometric relationship between the keels 112, 114 and the threaded bores 122, 124 constant and the sizes of the keels 112, 114 constant across each size of tibial component 102. A typical surgical kit would include augments 104 of several different thicknesses, such as three incrementally thicker augments with thicknesses of 5 mm, 10 mm and 15 mm, and different sizes. If the size of the keel clearance 160 and the geometric relationship between the keel clearance 160 and the through-bore 134 is maintained constant for all sizes of augments 104, and if the size of the keels 112, 113 and geometric relationship between the keels 112, 114 and threaded bores 122, 124 are constant for all sizes of tibial components 102, then all sizes of augments 104 should be able to be used interchangeably on all sizes of tibial components 102.

The components of the tibial system 10 may be made of standard materials for prosthetic implants. For example, a cobalt chrome alloy may be used. The exterior surfaces of the implant components are preferably textured for cemented implantation. However, the present invention is not limited to any particular material or surface finish unless expressly called for in the claims.

The components of the prosthetic system may have features as described in the following United States provisional patent applications filed on Sep. 9, 2002: application Ser. No. 60/409,284, entitled "PROSTHETIC TIBIAL COMPONENT WITH MODULAR SLEEVE" filed by Deborah S. German, Todd D. Durniak, Danny W. Rumple and Christel M. Klebba, (DEP 797); and application Ser. No. 60/409,262, entitled "DUO-FIXATION PROSTHIC JOINTS", filed by Brian Haas (DEP 799). These applications are incorporated by reference herein in their entireties. The United States patent applications filed concurrently herewith based upon and claiming priority to these provisional patent applications are also incorporated by reference herein in their entireties.

Figure 17:
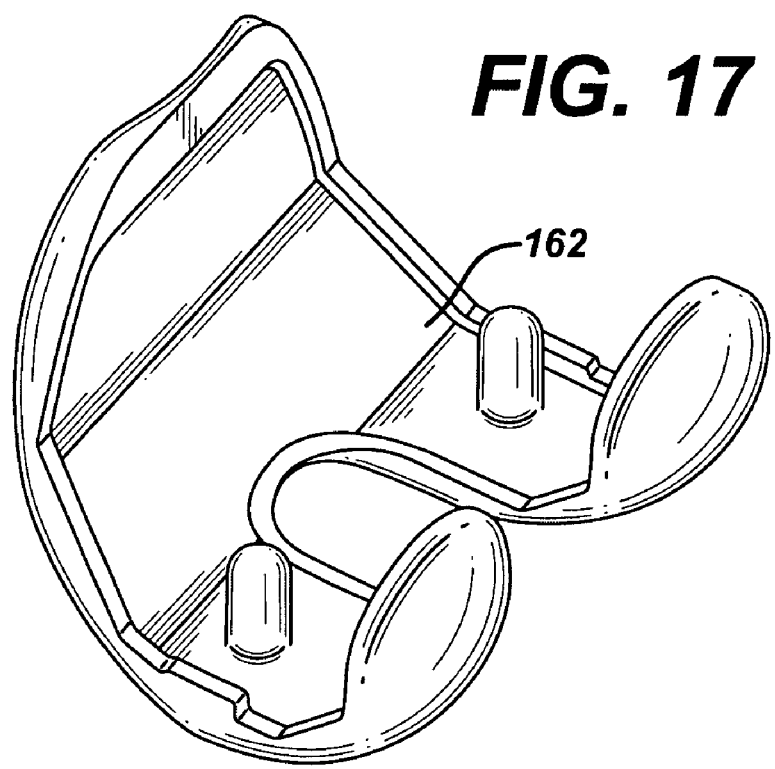
FIG. 17 is a perspective view of a femoral component that may be used with the tibial component and augment of the present invention.
Figure 18:
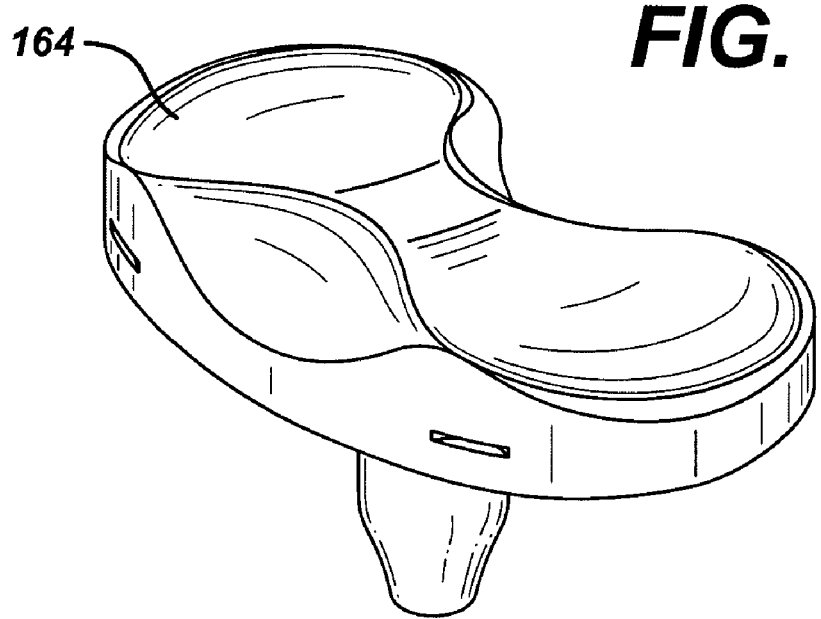
FIG. 18 is a perspective view of a tibial bearing insert that may be used with the tibial component and augment of the present invention and with the femoral component of FIG. 17.

The tibial system components can be provided as parts of a surgical kit. The kit may also include femoral components and tibial bearings. An example of a suitable femoral component is illustrated at 162 in FIG. 17. An example of a suitable tibial bearing is illustrated at 164 in FIG. 18.

Figure 15:
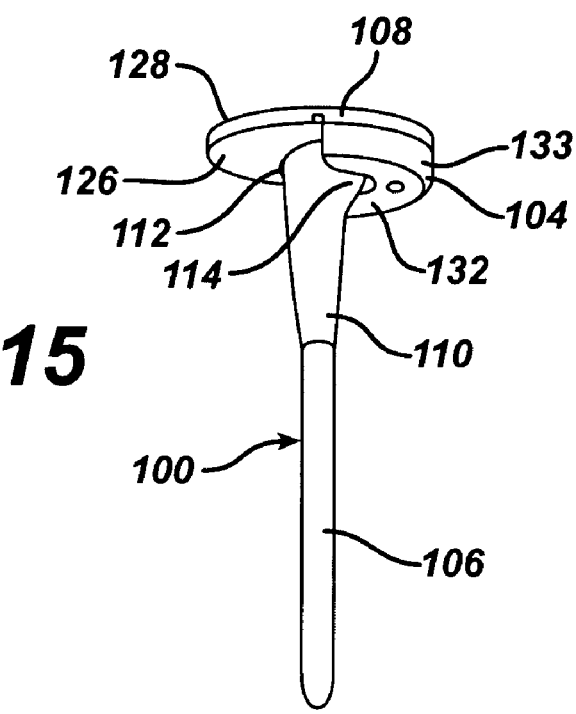
FIG. 15 is a perspective view illustrating the universal tibial augment of FIGS. 12–13 mounted on one side of the central plane of the tibial tray.
Figure 16:
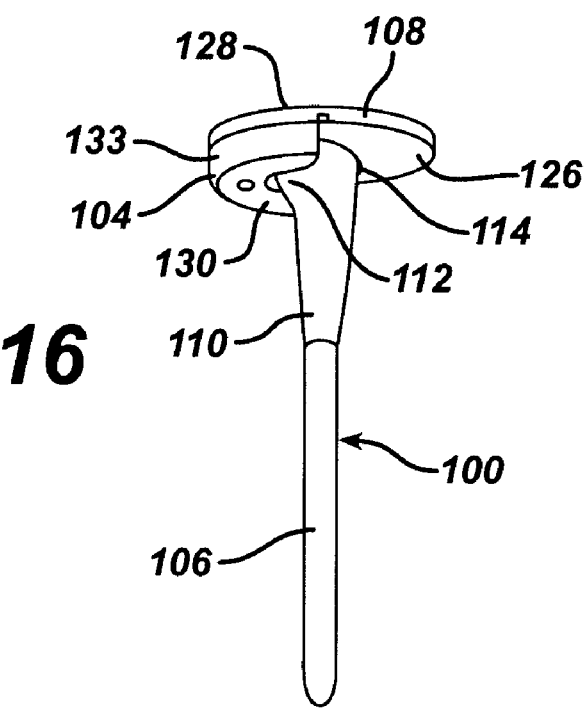
FIG. 16 is a perspective view illustrating the same universal tibial augment of FIGS. 12–13 and 15 mounted on the opposite side of the central plane of the tibial tray.

In using the tibial system of the present invention, the surgeon uses conventional surgical techniques to prepare the patient's knee and to prepare the bone surfaces to receive the prosthetic components. If during the procedure the surgeon determines that it is necessary to resect more bone from either the medial or lateral proximal tibia, the surgeon then selects an augment 104 of appropriate thickness to use with the tibial component 102. If the additional resection was on the medial side, the surgeon places the augment 104 on the medial side of the tibial component 102, with the first surface 130, for example, against the distal surface 126 of the tibial tray 108, and inserts a screw into through the second countersink 138 of the augment 104. The screw is pushed through the entire smooth through-bore 134, including the neck 140 and opposite countersink 136, until the threads of the screw engage the threads of the threaded bore 122 or 124 of the tibial tray 108. The assembled augment 104 and tibial component is illustrated in FIG. 15. If instead the additional resection was on the lateral side, the surgeon can flip the same augment 104 over so that the second surface 132 is placed against the distal surface 126 of the tibial tray 108. The surgeon then inserts a screw into and through the first countersink 136, the smooth neck 140 and through the second countersink 138 until the threads of the screw engage the threads of the threaded bore 122 or 124 of the tibial tray 108. In both cases, the augment 104 is mounted to the tibial tray 108 by the engagement of the screw threads with the threads of the threaded bore 122 or 124 in the tibial tray 108 and the engagement of the head of the screw against the inner surface of one of the countersinks 136, 138 of the augment 104. The assembled augment and tibial component would then appear as illustrated in FIG. 16.

Since the augments of the present invention are universal, and capable of use on either the medial or lateral side of the tibial component, the surgical kit can contain fewer augments, reducing inventory and lowering costs. The term "universal" includes tibial augments that can be used on the medial, lateral, posterior or anterior side of the distal surface of the tibial tray, either because the tibial augment is reversible as illustrated or because the tibial augment is shaped for use on any of the four sides of the tibial component without being reversed.

Although the invention has been illustrated for use in a prosthetic knee system, and more particularly for use with the tibial components of a prosthetic knee system, it should be appreciated that the principles of the present invention may be applicable to other prosthetic joints. Moreover, while the illustrated embodiment of the invention may be particularly useful in revision surgery, the principles of the present invention may also find application in primary joint arthroplasties.

While only a specific embodiment of the invention has been described and shown, it is apparent that various alternatives and modifications can be made thereto. Moreover, those skilled in the art will also recognize that certain additions can be made to these embodiments. It is, therefore, the intention in the appended claims to cover all such alternatives, modifications and additions as may fall within the true scope of the invention.

We claim:

1. A universal tibial augment comprising:
    a first surface;
    a second surface;
    a thickness between the first surface and the second surface and a through-bore extending from the first surface to the second surface;
    wherein the through-bore has a central longitudinal axis and includes a first countersink at the first surface, a second countersink at the second surface and a smooth neck connecting the first and second countersinks;
    wherein the augment includes inner tapered surfaces defining the first and second countersinks and a smooth inner cylindrical surface defining the neck;
    wherein the shape and dimensions of the inner tapered surfaces defining the first and second countersinks are substantially the same; and
    wherein the augment is part of a kit, the kit further comprising: a tibial component, a tibial bearing and a femoral component.

2. The universal tibial augment of claim 1 wherein the augment comprises a tibial block.

3. The universal tibial augment of claim 1 wherein the first and second surfaces of the augment are substantially parallel to each other.

4. The universal tibial augment of claim 1 wherein the augment is reversible.

5. A prosthetic tibial system comprising:
    a tibial component including a tibial tray having a proximal side and a distal side and a stem extending outward from the distal side, wherein the tibial tray has a plane of symmetry extending through the stem and the proximal side, the tibial tray including a threaded bore on each side of the plane of symmetry extending from the distal side toward the proximal side; and
    a universal tibial augment for mounting on the distal side of the tibial tray, the tibial augment having a first side, a second side opposite the first side, a thickness between the first side and the second side and a through-bore extending from the first side to the second side;
    wherein the tibial augment is mountable on the distal surface of the tibial tray on both sides of the plane of symmetry of the tibial tray; and
    wherein the through-bore of the universal tibial augment has a central longitudinal axis and a plane of symmetry perpendicular to the central longitudinal axis.

6. The prosthetic tibial system of claim 5 wherein the tibial augment is mountable to the distal side of the tibial tray with the first side of the tibial augment against the distal side of the tibial tray and also mountable to the distal side of the tibial tray with the second side of the tibial augment against the distal side of the tibial tray.

7. The system of claim 5 wherein the augment includes a smooth inner cylindrical surface defining a reduced diameter neck in the through-bore.

8. The system of claim 5 wherein the first side of the augment is substantially parallel to the second side of the augment.

9. The system of claim 5 wherein the tibial augment is reversible.

10. The system of claim 5 wherein the system is part of a kit, the kit further comprising: a femoral component and a tibial bearing.

* * * * *